(12) United States Patent
Bruce et al.

(10) Patent No.: US 6,376,481 B2
(45) Date of Patent: *Apr. 23, 2002

(54) STEROL ESTERS IN TABLETED SOLID DOSAGE FORMS

(75) Inventors: Richard D. Bruce, Rydal; John D. Higgins, Ft. Washington; Stephen A. Martellucci, Mont Clare, all of PA (US)

(73) Assignee: McNeil-PPC, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/145,528

(22) Filed: Sep. 2, 1998

(51) Int. Cl.⁷ .......................... A61K 31/56; A61K 9/14; A61K 9/20; A61K 47/00
(52) U.S. Cl. ................ 514/169; 424/464; 424/465; 424/489; 514/769; 514/770; 514/951; 514/975
(58) Field of Search ................ 424/450, 464, 424/489, 493, 465; 514/169, 769, 770, 951, 975

(56) References Cited

U.S. PATENT DOCUMENTS

| | | | | |
|---|---|---|---|---|
| 3,004,043 A | 10/1961 | Stern | | 552/544 |
| 3,203,862 A | 8/1965 | Jones | | 514/78 |
| 3,495,011 A | 2/1970 | Fossel | | 514/547 |
| 3,865,939 A | * 2/1975 | Jandacek | | 514/182 |
| 3,881,005 A | 4/1975 | Thakkar et al. | | 514/182 |
| 4,160,850 A | 7/1979 | Hallstron et al. | | 426/601 |
| 4,195,084 A | 3/1980 | Ong | | 514/182 |
| 4,238,520 A | 12/1980 | Miller et al. | | 426/573 |
| 4,588,717 A | 5/1986 | Mitchell | | 514/170 |
| 4,705,875 A | 11/1987 | Mitchell | | 556/46 |
| 4,824,672 A | 4/1989 | Day et al. | | 424/738 |
| 4,831,058 A | * 5/1989 | Pankhania et al. | | 514/570 |
| 4,883,788 A | 11/1989 | Day et al. | | 514/57 |
| 5,306,514 A | 4/1994 | Letton et al. | | 426/531 |
| 5,306,515 A | 4/1994 | Letton et al. | | 426/531 |
| 5,308,639 A | 5/1994 | Fung | | 426/602 |
| 5,326,825 A | 7/1994 | Nasman et al. | | 525/301 |
| 5,338,563 A | 8/1994 | Mikulka et al. | | 426/604 |
| 5,472,728 A | 12/1995 | Miller et al. | | 426/601 |
| 5,502,045 A | 3/1996 | Miettinen et al. | | 514/182 |
| 5,514,398 A | 5/1996 | Imai et al. | | 426/271 |
| 5,629,359 A | * 5/1997 | Peeters et al. | | 522/96 |
| 5,747,464 A | 5/1998 | See | | 514/26 |
| 5,770,254 A | 6/1998 | Izzo et al. | | 426/633 |
| 5,932,562 A | * 8/1999 | Ostlund, Jr. | | 514/78 |
| 6,025,010 A | 2/2000 | Reddy | | 426/603 |
| 6,025,348 A | 2/2000 | Goto et al. | | 514/182 |
| 6,054,144 A | * 4/2000 | Burruano et al. | | 424/464 |
| 6,087,353 A | * 7/2000 | Stewart et al. | | 514/182 |
| 6,110,502 A | * 8/2000 | Burruano et al. | | 424/499 |
| 6,242,001 B1 | * 6/2001 | Bruce et al. | | 424/464 |

FOREIGN PATENT DOCUMENTS

| | | | |
|---|---|---|---|
| EP | 0 608 600 A1 | 3/1994 | |
| EP | 0 771 531 A2 | 7/1997 | |
| EP | 0 947 197 | 10/1999 | ......... A61K/31/575 |
| GB | 284 814 | 9/1972 | |
| GB | 1 413 102 | 5/1975 | |
| GB | 1 598 638 | 9/1981 | |
| WO | 95/00158 | 5/1995 | |
| WO | 96/38047 | 5/1996 | |
| WO | 98/06714 | 2/1998 | |
| WO | WO 99/56729 | 11/1999 | |
| WO | WO 99/63841 | 12/1999 | |

OTHER PUBLICATIONS

Editors: Wade, Ailey and Weller, Paul J.; Polyoxyethylene Sorbitan Fatty Acid Esters and Sorbitan Esters (Sorbitan Fatty ACid Esters); Handbook of Pharmaceutical Excipients, 2nd Edition, 1994, pp. 375–378 and pp. 473–476, respectively.

U.S. application No. 09/025,952, filed Feb. 9, 1998. Status Allowed—"Method for Producing Water Dispersible Sterol Formulations".

U.S. application No. 09/185,788, filed Nov. 4, 1998. Status Allowed—Issue fee Paid Jan. 11, 2000—"Method for Producing Water Dispersible Sterol Formulations".

U.S. application No. 09/200,623, filed Nov. 30, 1998. Status Pending—"Method for Producing Dispersible Sterol and Stanol Compounds".

Slover et al., "Lipids in Margarines and Margarine–Like Foods", JAOCS, vol. 62, 4/95.

Westrate and Meijer, "Plant sterol–enriched margarines and reduction of plasma total– and LDL–cholesterol concentrations in normocholesterolaemic and mildly hypercholesterolaemic subjects", Eur. J. of Clin. Nut., 1998.

* cited by examiner

*Primary Examiner*—Jose' G. Dees
*Assistant Examiner*—Frank Choi
(74) *Attorney, Agent, or Firm*—Timothy E. Tracy

(57) ABSTRACT

The present invention provides a sterol, stanol or their corresponding acid ester in a form suitable for the manufacture of an oral dosage form. A method for producing the oral dosage form is also provided.

8 Claims, No Drawings

STEROL ESTERS IN TABLETED SOLID DOSAGE FORMS

FIELD OF THE INVENTION

The present invention relates to sterol ester in the form of a tablet that is suitable for reducing cholesterol levels in patient.

BACKGROUND OF THE INVENTION

Several reports have described the use of plant-sterols (i.e., β-sitosterol) as dietary supplements for the reduction of serum cholesterol levels. It is generally accepted that the sitosterol family of plant sterols reduces serum cholesterol by inhibiting the intestinal absorption of cholesterol. More recently, β-sitosterol's saturated equivalent, β-sitostanol, has been shown to be more effective in the reduction of intestinal cholesterol absorption. Furthermore, sitostanol itself is virtually unabsorbed, so it does not contribute at all to in vivo serum cholesterol concentration upon consumption. These observations make β-sitostanol an attractive candidate as a dietary supplement for reduction of serum cholesterol levels.

Typically it has been necessary to incorporate the sterol ester in a suitable material such as a margarine, in which the waxy nature of the sterol ester can be tolerated. There have been reports that describe how the esterification of sterols (stanols) to a fatty acid or an edible oil produces a sterol (stanol) ester with improved micelle solubility characteristics. For example, when sitostanol is esterified to edible oil such as rapeseed oil, a wax-like mixture of fatty acid esters with excellent lipid solubility results. These sterol esters are conveniently incorporated into food products such as margarine.

However there is a continuing need for a tableted form of the sterol ester.

SUMMARY OF THE INVENTION

The present invention is directed to a solid oral dosage form having a compressed free-flowing powder, which includes an effective amount of sterol, stanol or their corresponding acid ester to reduce cholesterol, about 5 to about 75 milligrams per dosage form of a support with a surface area range of from about 100 to 350 square meters/gram, wherein the sterol, stanol or their corresponding acid ester is in a molten form when loaded onto the support, and a monofunctional surfactant and a polyfunctional surfactant, wherein the polyfunctional surfactant is a polyoxyethylene derivative of the monofunctional surfactant.

The present invention also provides a method for producing a solid oral dosage form that includes heating a sterol, stanol or their corresponding acid ester at a temperature of from about 45 to about 100° C. to provide the sterol, stanol or their corresponding acid ester in a molten form, providing a monofunctional surfactant and a polyfunctional surfactant, wherein the polyfunctional surfactant is a polyoxyethylene derivative of the monofunctional surfactant, admixing the molten sterol, stanol or their corresponding acid ester and the monofunctional surfactant and the polyfunctional surfactant to form a sterol, stanol or their corresponding acid ester-surfactant mixture, providing a support with a surface area of from about 100 to about 350 square meters per gram, adding a sufficient amount of the support to the molten sterol, stanol or their corresponding acid ester-surfactant mixture to form a flowable powder, and optionally compressing the flowable powder to form a tablet.

DETAILED DESCRIPTION OF THE INVENTION

β-sitosterols are typically derived from wood or agricultural sources, such as soy based mixtures. In addition to β-sitosterol, as used throughout this application, β-sitosterol is also understood to include the esters of β-sitosterols, as well the stanol and stanol ester forms which are the oxidized form of the sterols. These derivatives are well known in the art and include patents U.S. Pat. No. 5,244,887; U.S. Pat. No. 5,502,045 and U.S. Pat. No. 5,698,527. . In order to be effective in reducing cholesterol in the bloodstream, it is necessary to consume less about 1.5 grams, typically from about 0.25 to about 1.4 grams, preferably from about 0.5 to about 1.2 and more preferably from about 0.8 to about 1 gram of β-sitosterol per dose.

The present invention is directed to a solid oral dosage form comprising: a support with a surface area range from about 100 to 350 square meters/gram; an effective amount of stanol ester provided to reduce cholesterol; an effective amount of a mixed micelle surfactant system.

The present invention also provides a method for producing a solid dosage form comprising: providing the sterol ester in a molten form; providing an effective amount of surfactant; admixing the sterol ester and the surfactant; providing a support with a surface area of form about 100 to about 350 square meters per gram; adding a sufficient amount of the support to the sterol ester, surfactant mixture to form a flowable powder; and optionally compressing the flowable powder to form a tablet.

The above described method uses the phase change from solid to liquid form under elevated temperature to load the sterol ester onto support followed by a second phase change when the mixture is cooled to room temperature to help preserve adsorbate's physical integrity.

The present invention provides a stanol material in a form suitable for the manufacture of an oral dosage. A method for producing the stanol material is also provided.

The present invention is applicable to any of the following serum cholesterol lowering compounds, including stanols, sterols, sterol esters, stanol esters, β-sitosterol, β-sitostanol and the like. Those with skill in the art will be able to carry out the present invention with any of these related materials.

In order to be most effective when ingested, the particle size of the β-sitosterol should be in the range of from 10 to 40 microns. More preferably the particle size should from about 20 to 35 microns. Any grinding technique known in the art may be used to grind the β-sitosterol. Suitable methods include pulverizing, rotary hammermill, air milling and the like of which air milling is most preferred. Smaller particle sizes are preferred in that the resulting β-sitosterol product is more readily exposed to bile salts in the digestive tract. The handling properties of the smaller particle size product are less desirable, resulting in higher angle of rupture, higher angle of repose and compressibility. The handling of the water-dispersible βsitosterol product can be improved with increased particle size; however, this is believed to be detrimental to the efficacy of the β-sitosterol in reducing serum cholesterol.

In order to form the water dispersible β-sitosterols appropriate surfactants are required. The present invention employs a dual surfactant system. One surfactant in the system is monofunctional, while the second surfactant is polyfunctional. The monofunctional surfactants tend to be more hydrophobic, whereas the polyfunctional surfactants tend to be hydrophilic. The two-surfactant system employed in this invention creates a mixed micelle system that results in the water-dispersible product. As used herein monofunctional is defined as the ability of the surfactant to bond to the β-sitosterol. The polyfunctional surfactant has the ability to bond to the β-sitosterol as well as to the other surfactant.

Useful surfactants in the practice of the present invention include polyglycerol esters, polysorbates, mono and diglycerides of fatty acids, propylene glycol esters, sucrose fatty acid esters and polyoxyethylene derivatives of sorbitan fatty acid esters. These surfactants are well known in the art and are commercially available.

Suitable polyglycerol esters include triglyceryl monostearate, hexaglyceryl distearate, hexaglyceryl monopalimate, hexaglyceryl dipalmitate, decaglyceryl distearate, decaglyceryl monoleate, decaglyceryl dioleate, decaglycerol monopalmitate, decaglycerol dipalmitate, decaglyceryl monostearate, octaglycerol monoleate, octaglycerol monostearate and decaglycerol monocaprylate.

Other useful surfactants include polysorbates made from the reaction product of monoglycerides or sorbitan esters with ethylene oxides. Examples of useful polysorbates include polyoxyethylene 20 mono- and diglycerides of saturated fatty acids, polyoxyethylene 4 sorbitan monostearate, polyoxyethylene 20 sorbitan tristearate, polyoxyethylene 20 sorbitan monooleate, polyoxyethylene 5 sorbitan monooleate, polyoxyethylene 20, sorbitan trioleate, sorbitan monopalmitate, sorbitan monolaurate, propylene glycol monolaurate, glycerol monostearate, diglycerol monostearate, glycerol lactyl-palmitate.

Other suitable surfactants include, with HLB values provided in brackets, [ ], include decaglycerol monolaurate [15.5]; decaglycerol distearate [10.5]; decaglycerol dioleate [10.5]; decaglycerol dipalmitate [11.0]; decaglycerol monostearate [13.0]; decaglycerol monoleate [13.5]; hexaglycerol monostearate [12.0]; hexaglycerol monoleate [10.5]; hexaglycerol monoshortening [12.0]; polyoxyethylene (20) sorbitan monolaurate [16.7]; polyoxyethylene (4) sorbitan monolaurate [13.3]; polyoxyethylene (20) sorbitan monopalmitate [15.6]; polyoxyethylene (20) sorbitan monostearate [14.9]; polyoxyethylene (20) sorbitan tristearate [10.5]; polyoxyethylene (20) sorbitan monooleate [15.0]; polyoxyethylene (5) sorbitan monooleate [10.0]; polyoxyethylene (20) sorbitan trioleate [11.0]. As is appreciated by those with skill in the art, the HLB value for a surfactant is an expression of its Hydrophile-Lipophile balance, i.e., the balance of the size and strength of the hydrophilic (polar) and lipophilic (non-polar) groups of the surfactant.

Lactic acid derivatives include sodium stearoyl lactylate and calcium stearoyl lactylate.

The level of monofunctional surfactant is typically from about 1 to about 15 weight percent based upon the final dried weight of the β-sitosterol product, preferably from about 2 to about 12, and most preferably about 4 to about 10 weight percent. The level of polyfunctional surfactant is typically from about 0.5 to about 15 weight percent based upon the final dried weight of the β-sitosterol product, preferably from about 2 to about 12, and most preferably about 4.0 to about 10 weight percent. TWEEN 80 is the preferred monofunctional surfactant and SPAN 80 is the preferred polyfunctional surfactant. Suitable ratios of monofunctional/polyfunctional surfactants which form the mixed micelle include from about 1:6 to about 1.5:1, preferably from about 1:4 to about 1.3:1, most preferably about 1:1 ratio. The level of surfactant employed ranges from about 0.5 to about 8 percent by weight total surfactant system, preferably 1 to about 6, most preferably from about 3 to about 4 percent by weight.

It has long been known that increasing the concentration of surfactant in a co-crystallization of a poorly water-soluble drug leads to an increase in wettablity. This is has also been found to improve the dissolution of the active ingredient.

The present invention also employs a support surface with a high surface area. The support is a pharmaceutically acceptable material with the specified surface area. The support surface typically has a surface area of from about 100 to about 450 square meters, preferably from about 150 to about 400 and most preferably from about 200 to about 350 square meters per gram. The support can be an organic (carbon and hydrogen containing) such as xantham gum, microcrystalline cellulose, or excipient used for tablet formation, or preferably the support surface is an inorganic material (containing materials other than carbon and hydrogen), most preferably selected from magnesium aluminosilicate, tricalcium phosphate, silicon dioxide and the like.

The support is provided in an amount sufficient to form a flowable powder, which is typically provided in an amount ranging from about 5 to about 75 milligram per tablet, preferably from 50 to about 10 and most preferably from about 40 to about 20 mg per tablet produced.

The present invention also contemplates the inclusion of pharmaceutical ingredients including, sweeteners, disintegrants lubricants, fillers, binders and adhesives, excipients, colors, preservatives and the like.

The present invention employs a phase change of the sterol ester from solid to molten forms under elevated temperature to load the sterol ester onto the solid support followed by a second phase change when the mixture is cooled to room temperature to help preserve the tablets physical integrity. Typically the sterol ester is heated to a temperature of from about 100 to about 45° C., preferably from about 70 to about 50 and most preferably from about 62 to about 56° C.

One technique for the measurement of the effectiveness of the sterol ester system is through the size of the resulting micelles formed when placed into water. The size of the micelles formed in the suspension may be measured through the use of a Turbimeter. The greater turbidity, the larger the micelle formation. It is expected that greater turbidty, i.e., larger micelles provides a more effective form of the β-sitosterol for reducing cholesterol when consumed. Preferred turbidity levels are greater than about 1250, preferably greater than 2500 and most preferably greater than 3000 Nepthialic Turbidity Units (NTU). As used herein turbidity is understood to be the same as defined by the United States Pharmacopeia, the light scattering effect of suspended particles and turbidity as the measure of the decrease in the incident beam intensity per unit length of a given suspension. The range of turbidty values is from 0 to 20,000 NTU. As a point of reference the turbidity of water is zero. The turbidity of the samples was measured at room temperature.

After the sterol ester is mixed with the catalyst support, the mixture is allowed to cool to room temperature once again allowing the material to solidify. The solidified material is then mixed with suitable materials and is ready for tableting. Tableting is accomplished by techniques well known in the art, which include slugging, Chilsonation and rotary tablet compression. Tablets are understood to include gelatin-coated materials, caplets, capsules and the like.

One advantage of this invention is that it offers a tamper-resistant, consumer-appealing tablet form in which a minimum quantity of excipients is needed. Another advantage of this invention is the potential for enhanced bioavailability of the sterol ester. Since the mechanism of sterol ester's cholesterol reduction efficacy is thought to involve incorporation into the GI micelle, any dosage form must deliver a rapidly dispersible molecular state. This is ensured by delivery of a solid solution of sterol esters and surfactants, which is a molecular dispersion. Solid dispersions of poorly water-soluble drugs have been shown to enhance in vitro dissolution rates and in vivo bioavailability. Another advantage is the simple, one container preparation that is rapid and economical.

The following examples are provided to illustrate the present invention. The present invention is not limited to the embodiments provided below. Unless noted otherwise all units are understood to be in weight percent.

EXAMPLE 1
Preparation of Solid Supported Sterol ester using preferred surfactant blend Stanol Ester (Rasio) was melted in a hot-water jacketed beaker. A mixed micelle liquid surfactant system was added to the molten product and stirred until homogeneous. In this example, a Tween 80/Span 80 mixture (ICI Chemicals) was added in a 1:1 ratio. Portions of Magnesium Aluminosilicate (Neusilin US2) or Tricalcium Phosphate were added with stirring and the resultant effect on bulk properties monitored from suspension, to paste through granulation until a dry, free-flowing powder (A) resulted with a final weight % example composition being preferred as 52.9% stanol ester, 10.1% Tween 80, 10.6% Span 80 and 26.5% Neusilin US2. The mixture was removed from the beaker and allowed to cool. Mixture exhibited excellent powder flow, wetted & dispersed spontaneously upon addition to room temperature tap water.

COMPARATIVE EXAMPLE
Preparation of Solid Supported stanol ester using incorrect surfactant blend A mixture prepared in a method similar to Example 1 was made substituting Tween 40 for Tween 80 (both available form ICI Americas). Mixture exhibited excellent powder flow but did not wet or disperse upon addition to room temperature water. This illustrates importance of mixed micelle surfactant system in this invention.

EXAMPLE 2
Prototype of directly compressible, swallowable stanol ester tablet A portion of Example 1 product was powder-blended with 20% weight sodium starch glycolate. The new mixture was manually compressed to 2000 lbs. force for about 3 seconds on a Carver hydraulic press using $^{11}/_{16}$ round, flat-faced beveled-edge tooling. Test tablets contained 418 mg as free stanol. Compacts ejected with surprisingly little frictional force. Tablets produced showed spontaneous surface erosion and were about 10% dispersed after standing one minute in unstirred deionized water at room temperature.

EXAMPLE 3
Prototype of directly compressible chewable tablet

A portion of the material made in Example 1 was powder blended with xylitol, aspartame and artificial Watermelon Strawberry flavoring. The mixture was compressed under identical conditions as in Example 2 to swallowable tablet prototype. Tablets again ejected without difficulty, in the absence of any additional lubrication. A solid dispersion (solid solution mixtures of active(s) with amphiphilic inert semi-solid excipient(s)) of Example 1 was made in a carrier (e.g., polyethylene glycol, saturated polyglycolized glycerides, waxes, oils, microemulsions) which is water soluble and solid/semi solid at room temperature yet liquid at elevated temperature. The active ingredient, is first dissolved in molten vehicle. This melt is then hot filled into either hard-shell capsules or soft-gels using existing technology. After filling, the mixture solidifies upon cooling; creating a solid or semi solid filled capsule product.

EXAMPLE 4

A comparison study of the effects of various adsorbate supports on the final tableted form was performed using Neusilin (Magnesium Aluminum Silicate), Tixosil (silicon dioxide) and Tri-Cal (Tricalcium Phosphate) to create Stanol Ester Adsorbate (SEA).

Preparation of stanol ester adsorbate: An accurately weighed amount of the stanol ester (Rasio Sito-74) was placed into a heated water jacketed beaker (hot water circulator) equilibrated at 57 ° C. The stanol ester was then allowed to melt into the liquid phase. When the stanol ester was completely melted, small portions of an adsorbate were slowly stirred into the liquid. The adsorbate material was continuously added until the stanol ester liquid was completely incorporated onto the adsorbate. The resulting material formed either a free-flowing powder or large granules.

Milling of stanol ester adsorbate granules: The stanol ester adsorbate granules were dried in a hood for 15–30 minutes before milling. After the granules were dried, liquid nitrogen was poured into a micro-mill (Scienceware). The granules were then placed into the mill and frozen with more liquid nitrogen. Finally, the top of the mill was replaced and the granules were milled into a fine powder.

Dry mixing of the tablet formulations: Dry mixing of the active and excipients in a whirl-pak bag prepared all tablet formulations. The excipients in each formulation were accurately weighed on a balance, dry mixed with a spatula in a weigh boat and then transferred to a whirl-pak for continued dry mixing.

Tablet pressing: The dry mixed formulations were poured into an $^{11}/_{16}$- inch round dye and pressed using an $^{11}/_{16}$-inch round FFBE tooling. The tablets were manually pressed for three seconds at 2000 psig with a Carver press.

Disintegration tests (DT): Tablets were placed in a calibrated disintegration bath containing 37° C. water. The tablets were repeatedly dunked in a 900 milliliter-water bath until completely disintegrated. This procedure was done visually and was timed with a stopwatch.

Turbidity tests: After the tablets were completely disintegrated in the DT above, the water was placed into a small glass tube and homogenized. The tube was then placed into a Hatch, 2100N Turbidimeter and a reading was taken. The Neusilin and Tixosil SEA's formed a free-flowing powder, where as the Tri-Cal SEA formed large granules. These large granules were then milled into a fine powder as described above.

Five different formulations, using the three SEA's above, were prepared and tableted as described in the above experimental. These formulations are shown in the Tables 1–5 below.

TABLE 1

Chewable tablet formulation using the Neusilin stanol ester adsorbate.

| Neusilin Stanol Ester Adsorbate %: | total active weight per tablet total number tablets total tablet weight | 500 mg (as Stanol) 11 tablets 2,400.0 mg |
|---|---|---|

TABLE 1-continued

| | | total tablet batch weight | 26.400 G | |
|---|---|---|---|---|
| Item | Tablet % | target mass (mg/tablet) | target mass (G/batch) | actual mass (G)/batch |
| Stanol Ester Adsorbate | 50.7 | 1,217 | 13.385 | 13.393 |
| Xylitol (xylitab) | 22.5 | 540 | 5.940 | 5.944 |
| Magnesium Stearate | 1.8 | 43 | 0.475 | 0.476 |
| Sodium Starch glycolate | 25 | 600 | 6.600 | 6.604 |
| | 100.0% | 2,400 | 26.400 | 26.417 |

The formulation in Table 1 was prepared using the Neusilin stanol ester adsorbate. As seen above, these tablets contain 500mg of the active stanol and have a large amount of sodium starch glycolate (25%). After pressing, the resulting tablets were slightly sticky on one side, but didn't film or stick to the tooling. Dissolution times were run on four of the tablets, which completely disintegrated between 12 min 43 seconds and 13 min 47 seconds. The resulting solution gave a turbidity of 1253 NTU. The formulation in Table 2 was prepared using the Tixosil stanol ester adsorbate. The resulting tablets contained 500 mg of active stanol and a large amount of sodium starch glycolate (25.7%). After pressing, the tablets ejected nicely and left no noticeable filming disintegration times were run on four of the tablets, which completely disintegrated between 3 min 54 seconds and 4 min 05 seconds. The turbidity of the solution was measured at 4398 NTU.

TABLE 2

Chewable tablet formulation using the Tixosil stanol ester adsorbate.

| Tixosil Stanol Ester Adsorbate %: | Total active weight per tablet | 500 mg (as Stanol) |
| --- | --- | --- |
| | Total number tablets | 11 tablets |
| | Total tablet weight | 2,400.0 mg |
| | Total tablet batch weight | 26.400 G |

| Item | Tablet % | target mass (mg/tablet) | target mass (G/batch) | actual mass (G)/batch |
|---|---|---|---|---|
| Stanol Ester Adsorbate | 50 | 1,200 | 13.200 | 13.241 |
| Xylitol (xylitab) | 22.5 | 540 | 5.940 | 5.938 |
| Mg Stearate | 1.8 | 43 | 0.475 | 0.476 |
| Sodium Starch glycolate | 25.7 | 617 | 6.785 | 6.774 |
| | 100.0% | 2,400 | 26.400 | 26.429 |

TABLE 3

Chewable tablet formulation using the Tri-calcium phosphate stanol ester adsorbate.

| Tri-calcium Phosphate Stanol Ester 46.3% Adsorbate %: | total active weight per tablet | 400 mg (as Stanol) |
| --- | --- | --- |
| | total number tablets | 11 tablets |
| | total tablet weight | 2,400.0 mg |
| | total tablet batch weight | 26.400 G |

| Item | lot # | Tablet % | target mass (mg/tablet) | target mass (G/batch) | actual mass (G/batch) |
|---|---|---|---|---|---|

TABLE 3-continued

| Stanol Ester Adsorbate | | 60 | 1,440 | 15.840 | 15.838 |
|---|---|---|---|---|---|
| Xylitol (xylitab) | | 4.6 | 110 | 1.214 | 1.213 |
| Mg Stearate | | 1.8 | 43 | 0.475 | 0.482 |
| Sodium Starch Glycolate | | 33.6 | 806 | 8.870 | 8.880 |
| | Totals | 100.0% | 2,400 | 26.400 | 26.413 |

The formulation in Table 3 was prepared with the Tri-calcium phosphate stanol ester adsorbate. The tablets contained 400 milligrams of active stanol and a large amount of sodium starch glycolate. The tablets were not sticky and they also didn't leave a film on the tooling. Dissolution times were run on four tablets, which completely disintegrated in 2 minutes and 08 seconds. The resulting 10 turbidity was 3136 NTU.

The formulation shown in Table 4 was prepared with the Neusilin stanol ester adsorbate. This formulation was done with a smaller amount of sodium starch glycolate (8%), a larger amount of sugar excipient and was pressed into a smaller tablet than the formulation in Table 1. A DT was performed on one of these tablets, which completely disintegrated in 27 minutes and 51 seconds.

TABLE 4

Chewable tablet formulation using the Neusilin stanol ester adsorbate.

| Neusilin Stanol Ester Adsorbate %: | total active weight per tablet | 501 mg (as Stanol) |
| --- | --- | --- |
| | total number tablets | 4 Tablets |
| | total tablet weight | 2,000.0 Mg |
| | total tablet batch weight | 8.000 G |

| Item | Tablet % | target mass (mg/tablet) | target mass (G/batch) | actual mass (G)/batch |
|---|---|---|---|---|
| Stanol Ester Adsorbate | 61 | 1,220 | 4.880 | 4.885 |
| Xylitol (xylitab) | 29.2 | 584 | 2.336 | 2.338 |
| Mg Stearate | 1.8 | 36 | 0.144 | 0.143 |
| Sodium Starch Glycolate | 8 | 160 | 0.640 | 0.643 |
| | 100.0% | 2,000 | 8.000 | 8.009 |

TABLE 5

Chewable tablet formulation using the Tri-calcium phosphate stanol ester adsorbate.

| Tri-calcium Phosphate) Stanol Ester 46.3% Adsorbate %: | total active weight per tablet | 500 mg (as Stanol) |
| --- | --- | --- |
| | total number tablets | 1 Tablets |
| | total tablet weight | 2,600.0 Mg |
| | total tablet batch weight | 2.600 G |

| Item | Tablet % | target mass (mg/tablet) | target mass (G/batch) | Actual mass (G/batch) |
|---|---|---|---|---|
| Stanol Ester Adsorbate | 69.2 | 1,799 | 1.799 | 1.800 |
| Xylitol (xylitab) | 10 | 260 | 0.260 | 0.264 |
| Mg Stearate | 1.8 | 47 | 0.047 | 0.047 |
| Sodium Starch Glycolate | 8 | 208 | 0.208 | 0.205 |

TABLE 5-continued

| | | | | | |
|---|---|---|---|---|---|
| Tri-Calcium Phosphate | | 11 | 286 | 0.286 | 0.287 |
| | Totals | 100.0% | 2,600 | 2.600 | 2.603 |

The formulation shown in Table 5 was prepared with the Tri-calcium phosphate SEA. This formulation is different from the one in Table 3 due to its smaller amount of sodium starch glycolate (8%) and its tri-calcium phosphate excipient. This formulation also differed in size (2.6 g) and by amount of active stanol (500 mg). A disintegration test was performed on one of the tablets, which disintegrated in 4 minutes and 29 seconds. The resulting turbidity was 924 NTU.

The formulations above show that it is possible to make a stanol ester chewable tablet, which could be dispersed in an aqueous solution under 30 min. These formulations, when compared, by dispersion time, stickiness and limited use of expensive excipients, to previous formulations, are clearly the best. From the five formulations above, the one shown in Table 5 is the most feasible. Tri-calcium phosphate is cheap, readily available and that this formulation uses a relatively small amount of sodium starch glycolate. Furthermore, the tablets made from this formulation completely dispersed into water after 4.5 minutes. An improvement was realized by combining the superior powder flow of Neusilin-based formulas and the more rapid disintegration times of the Tri-Cal based formulations.

We claim:

1. A solid oral solid dosage form comprising
   a compressed free-flowing powder comprising
   an effective amount of sterol, stanol or their corresponding acid ester to reduce cholesterol,
   about 5 to about 75 milligrams per dosage form of a support with a surface area range of from about 100 to 350 square meters/gram, wherein the sterol, stanol or their corresponding acid ester is in a molten form when loaded onto the support, and
   a monofunctional surfactant and a polyfunctional surfactant, wherein the polyfunctional surfactant is a polyoxyethylene derivative of the monofunctional surfactant.

2. The oral dosage form of claim 1 wherein the support is an inorganic material.

3. The oral dosage form of claim 2 wherein the support is selected from the group consisting of magnesium alumina silicate, silicon dioxide and tricalcium phosphate.

4. The oral dosage form of claim 1 wherein the stanol ester is provided in an amount of less than about 1.5 grams.

5. A method for producing a solid oral dosage form comprising:
   heating a sterol, stanol or their corresponding acid ester at a temperature of from about 45 to about 100° C. to provide the sterol, stanol or their corresponding acid ester in a molten form;
   providing a monofunctional surfactant and a polyfunctional surfactant, wherein the polyfunctional surfactant is a polyoxyethylene derivative of the monofunctional surfactant;
   admixing the molten sterol, stanol or their corresponding acid ester and the monofunctional surfactant and the polyfunctional surfactant to form a sterol, stanol or their corresponding acid ester-surfactant mixture;
   providing a support with a surface area of from about 100 to about 350 square meters per gram;
   adding a sufficient amount of the support to the molten sterol, stanol or their corresponding acid ester-surfactant mixture to form a flowable powder;
   and optionally compressing the flowable powder to form a tablet.

6. The method of claim 5 wherein the support is an inorganic material.

7. The method of claim 5 wherein the support is selected from the group consisting of magnesium alumina silicate, silicon dioxide and tricalcium phosphate.

8. The method of claim 5 wherein the sterol, stanol or their corresponding acid ester is provided in an amount of less than about 1.5 grams.

* * * * *